United States Patent
Bourrie et al.

(12) 
(10) Patent No.: US 6,642,258 B1
(45) Date of Patent: Nov. 4, 2003

(54) USE OF CENTRAL CANNABINOID RECEPTOR ANTAGONIST FOR PREPARING MEDICINES

(75) Inventors: Bernard Bourrie, Saint Gely du Fesc (FR); Pierre Casellas, Montpellier (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/088,704

(22) PCT Filed: Sep. 27, 2000

(86) PCT No.: PCT/FR00/02662

§ 371 (c)(1),
(2), (4) Date: Mar. 21, 2002

(87) PCT Pub. No.: WO01/24798

PCT Pub. Date: Apr. 12, 2001

(30) Foreign Application Priority Data

Oct. 1, 1999 (FR) .............................................. 99 12415

(51) Int. Cl.⁷ ............................................. A61K 31/445
(52) U.S. Cl. ....................................... 514/327; 514/903
(58) Field of Search ......................................... 514/327

(56) References Cited

U.S. PATENT DOCUMENTS 5,624,941 A    4/1997    Barth et al.

FOREIGN PATENT DOCUMENTS

| EP | 0 656 354 A1 | 6/1995 |
| EP | 0 860 168 A2 | 8/1998 |
| WO | 96/02248 | 2/1996 |
| WO | 00/15609 | 3/2000 |
| WO | 00/46209 | 8/2000 |

OTHER PUBLICATIONS

Pertwee, Roger G.; Current Medicinal Chemistry (Aug. 1999), vol. 6, No. 8, pp 635–664.

Consroe, Paul; Neurobiology of Disease (1998), vol. 5, pp 534–551.

Nagayama, T. et al; The Journal of Neuroscience (Apr. 15, 1999), vol. 19, No. 8, pp2987–2995.

Molina–Holgado, F.et al; FEBS Letters 433, (1998), pp 139–142.

Derwent Patent Abstract No. 199838 Aug. 1998.

Derwent Patent Abstract No. 200024, Mar. 2000.

Derwent Patent Abstract No. 200049 Aug. 2000.

*Primary Examiner*—Rebecca Cook
(74) *Attorney, Agent, or Firm*—Michael D. Alexander

(57) ABSTRACT

The invention relates to the use of a central cannabinoid receptor antagonist for the preparation of medicinal products that are useful in treating and preventing neuroinflammatory pathologies.

16 Claims, No Drawings

USE OF CENTRAL CANNABINOID RECEPTOR ANTAGONIST FOR PREPARING MEDICINES

This is a 371 of PCT/FR 10/02662 filed Apr. 27, 2000

The present invention relates to a novel use of a central cannabinoid receptor antagonist, referred to as $CB_1$ receptor antagonists.

More particularly, the invention relates to the use of a $CB_1$ receptor antagonist for the preparation of medicinal products intended for preventing and treating neuroinflammatory pathologies, in particular conditions involving demyelinization, such as multiple sclerosis or Guillain-Barré syndrome, for example, as well as viral encephalitis, cerebrovascular accidents or cranial trauma.

The effects of cannabinoids are due to a high-affinity interaction with specific receptors coupled to the G proteins. Two types of receptor are currently described: the $CB_1$ receptors, which are predominantly present in the central nervous system (Devane et al., Molecular Pharmacology, 1988, 34, 605–613) and the $CB_2$ receptors which are present in the immune system (Nye et al., The Journal of Pharmacology and Experimental Therapeutics, 1985, 234, 784–791; Kaminski et al., 1992, Molecular Pharmacology, 42, 736–742; Munro et al., Nature, 1993, 365, 61–65).

It is known that cannabis can reduce or suppress certain symptoms associated with multiple sclerosis, such as muscular spasticity and pain (CNS Drugs, 1999, 11/5, 327–334).

Moreover, it is described that compounds that are selectively active on the cannabinoid $CB_2$ receptors can be used in the treatment of inflammatory conditions of immune origin (patent application WO 98/31227).

The use of cannabinoid $CB_1$ receptor agonists is cited for the prevention and treatment of neurodegenerative conditions (patent application WO 98/439100).

N-Piperidino-5-(4-chlorophenyl)-1-(2,4-dichlorophenyl)-4-methylpyrazole-3-carboxamide, referred to hereinbelow as compound A, of formula:

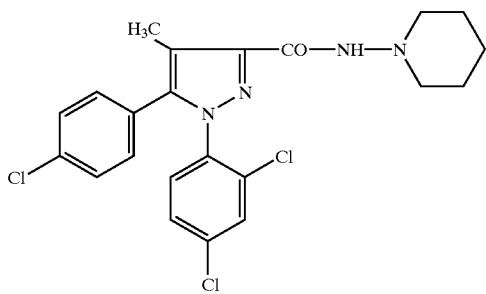

(I)

and the pharmaceutically acceptable salts and solvates thereof, are described in European patent EP-656 354 as cannabinoid $CB_1$ central receptor antagonists.

It has now been found that the administration of a $CB_1$ receptor antagonist such as compound A, pharmaceutically acceptable salts thereof or solvates thereof, is useful for preventing and treating neuroinflammatory pathologies, in particular conditions involving demyelinization, such as multiple sclerosis or Guillain-Barré syndrome, for example, as well as viral encephalitis, cerebrovascular accidents or cranial trauma.

According to one of its aspects, the present invention relates to the use N-piperidino-5-(4-chlorophenyl)-1-(2,4-dichlorophenyl)-4-methylpyrazole-3-carboxamide, a pharmaceutically acceptable salt thereof or a solvate thereof, for the preparation of medicinal products that are useful for preventing and treating such conditions.

Compound A and the pharmaceutically acceptable salts thereof are prepared according to European patent EP 656 354, and similarly the pharmaceutical compositions can be prepared according to the description of that same patent.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, erosols, implants, subcutaneous, transdermal, intramuscular, intravenous and intranasal administration forms and rectal administration forms.

The daily dose of the compound according to the invention is from 0.001 to 5 mg/kg, advantageously from 0.01 to 2.5 mg/kg and preferably from 0.02 to 2 mg/kg, to be administered in one or more dosage intakes. The compounds are generally formulated in a dosage unit containing from 0.1 to 500 mg, advantageously from 1 to 250 mg and preferably from 2 to 200 mg, of active principle per dosage unit, to be administered once, twice or several times simultaneously, according to need. Although these dosages are examples of average situations, there may be particular cases in which higher or lower dosages are appropriate, and such dosages also form part of the invention. According to the usual practice, the dosage which is appropriate for each patient is determined by the doctor according to the mode of administration, age, weight and response of the said patient.

According to the present invention, the oral administration forms are preferred.

The invention also relates to a method for treating neuroinflammatory pathologies, in particular conditions involving demyelinization, such as multiple sclerosis or Guillain-Barré syndrome, for example, as well as viral encephalitis, cerebrovascular accidents or cranial trauma.

The activity of the $CB_1$ cannabinoid receptor antagonist was investigated in the model of experimental allergic encephalitis (EAE) induced:

a) in Lewis rats by intraplantar administration of myelin basic protein (MBP) (fragment 68–84) in a Freund complete adjuvant (FCA) enriched with *Mycobacterium tuberculosis* according to the protocol published by Martin and Near (J. Neuroimmunol., 1995, 241–245), b) in SjL/j mice by subcutaneous administration of proteolipid peptide (PLP) (fragment 139–151) in a Freund complete adjuvant enriched with Mycobacterium tuberculosis according to the protocol described in Proc. Natl. Acad. Sci. USA, 1996, 93, 2499–2504. 24 and 48 hours after this injection, the mice receive a suspension of *Bordetella pertussis* intravenously.

EAE is an autoimmune and inflammatory condition of the central nervous system which presents demyelinizing lesions reminiscent, for example, of that of human multiple sclerosis.

In the experimental models, the representative compound according to the invention, administered orally or intraperitoneally from day zero of induction of the condition, very significantly attenuates the condition, the attenuation being measured both on the weight variation of the animals (the sick animals show a large loss of weight) and on the severity of the pathology (the sick animals show paralysis of the hind quarters). The weight loss of the animals treated with compound A is significantly smaller than that of the animals treated with the vehicle alone. Similarly, the severity of the condition is statistically smaller in the groups of animals treated with compound A.

The results of these studies show that the CB, cannabinoid receptor antagonist compound A and the pharmaceutically acceptable salts and solvates thereof, intervene favourably in this neurological dysfunction pathology and can thus be applied clinically in the treatment of conditions which cause demyelinizing lesions, such as multiple sclerosis.

EXAMPLE 1 Gel Capsule Containing a 1 mg Dose of $CB_1$ Receptor Antagonist

| | |
|---|---|
| Micronized compound A | 1.00 mg |
| Corn starch | 51.00 mg |
| Lactose monohydrate | 103.33 mg |
| Polyvidone | 4.30 mg |
| Sodium lauryl sulphate | 0.17 mg |
| Crosslinked sodium carboxymethyl cellulose | 8.50 mg |
| Purified water: qs for wet granulation | |
| Magnesium stearate | 1.70 mg |
| For a filled white opaque No. 3 gel capsule containing 170 mg | |

EXAMPLE 2 Gel Capsule Containing a 10 mg Dose of $CB_1$ Receptor Antagonist

| | |
|---|---|
| Micronized compound A | 10.00 mg |
| Corn starch | 51.00 mg |
| Lactose monohydrate | 94.33 mg |
| Polyvidone | 4.30 mg |
| Sodium lauryl sulphate | 0.17 mg |
| Crosslinked sodium carboxymethyl cellulose | 8.50 mg |
| Purified water: qs for wet granulation | |
| Magnesium stearate | 1.70 mg |
| For a filled white opaque No. 3 gel capsule containing 170 mg | |

EXAMPLE 3 Gel Capsule Containing a 30 mg Dose of $CB_1$ Receptor Antagonist

| | |
|---|---|
| Micronized compound A | 30.00 mg |
| Corn starch | 51.00 mg |
| Lactose monohydrate | 74.33 mg |
| Polyvidone | 4.30 mg |
| Sodium lauryl sulphate | 0.17 mg |
| Crosslinked sodium carboxymethyl cellulose | 8.50 mg |
| Purified water: qs for wet granulation | |
| Magnesium stearate | 1.70 mg |
| For a filled white opaque No. 3 gel capsule containing 170 mg | |

EXAMPLE 4 Gel Capsule Containing a 30 mg Dose of $CB_1$ Receptor Antagonist

| | |
|---|---|
| Micronized compound A | 30.00 mg |
| Lactose monohydrate | qs |
| Corn starch | 40.00 mg |
| Hydroxypropylmethyl cellulose 6 cP | 5.00 mg |
| Purified water: qs for wet granulation | |
| Crosslinked sodium carboxymethyl cellulose | 10.00 mg |
| Magnesium stearate | 2.00 mg |
| For a finished tablet containing 200 mg | |

What is claimed is:

1. A method for treating a neuroinflammatory pathology which comprises administering to a patient in need of said treatment an effective amount of N-piperidino-5-(4-chlorophenyl)- 1 -(2,4-dichlorophenyl)-4-methylpyrazole-3-carboxamide or a pharmaceutically acceptable salt or solvate thereof.

2. A method according to claim 1, for treating a neuroinflammatory pathology involving demyelinization, viral encephalitis, cerebrovascular accidents or cranial trauma.

3. A method according to claim 2 for treating a neuroinflammatory pathology involving demyelinization.

4. A method according to claim 3 for treating multiple sclerosis.

5. A method according to claim 3 for treating Guillain-Barré syndrome.

6. A method according to claim 2 for treating a neuroinflammatory pathology involving viral encephalitis.

7. A method according to claim 2 for treating a neuroinflammatory pathology involving cerebrovascular accidents.

8. A method according to claim 2 for treating a neuroinflammatory pathology involving cranial trauma.

9. A method for treating a neuroinflammatory pathology which comprises administering to a patient in need of said treatment an effective amount of N-piperidino-5-(4-chlorophenyl)- 1-(2,4-dichlorophenyl)-4-methylpyrazole-3-carboxamide.

10. A method according to claim 9 for treating a neuroinflammatory pathology involving demyelinization, viral encephalitis, cerebrovascular accidents or cranial trauma.

11. A method according to claim 10 or treating a neuroinflammatory pathology involving demyelinization.

12. A method according to claim 11 for treating multiple sclerosis.

13. A method according to claim 11 for treating Guillain-Barré syndrome.

14. A method according to claim 10 for treating a neuroinflammatory pathology involving viral encephalitis.

15. A method according to claim 10 for treating a neuroinflammatory pathology involving cerebrovascular accidents.

16. A method according to claim 10 for treating a neuroinflammatory pathology involving cranial trauma.

* * * * *